United States Patent [19]
Dodge et al.

[11] Patent Number: 5,468,773
[45] Date of Patent: Nov. 21, 1995

[54] METHODS FOR INHIBITING BONE LOSS AND CARTILAGE DEGRADATION USING WORTMANNIN AND ITS ANALOGS

[75] Inventors: Jeffrey A. Dodge, Indianapolis; Masahiko Sato, Carmel, both of Ind.

[73] Assignee: Eli Lilly and Company, Indianapolis, Ind.

[21] Appl. No.: 259,315

[22] Filed: Jun. 13, 1994

Related U.S. Application Data

[62] Division of Ser. No. 112,012, Aug. 25, 1993, abandoned.

[51] Int. Cl.$^6$ .................. A61K 31/365; A61K 31/34
[52] U.S. Cl. .................................. 514/453; 514/468
[58] Field of Search ..................... 549/275, 457; 514/453, 468

[56] References Cited

U.S. PATENT DOCUMENTS

| | | | |
|---|---|---|---|
| 3,668,222 | 6/1972 | Hauser | 549/275 |
| 5,378,725 | 1/1991 | Bonjouklian | 514/453 |

FOREIGN PATENT DOCUMENTS 91-3215423  1/1990  Japan.

OTHER PUBLICATIONS

Dewald, M. B. B., et al., *Br. J. Pharmacol.*, 69(2):269–270 (1980).
Bonser, R. W., et al., *Br. J. Pharmacol* 103(1):1237–1241 (1991).
Wiesinger, D., et al., *Experientia* 30(2):135–136 (1974).
Closse, A. et al., *J. Med. Chem.* 24(12):1465–1471 (1981).
Reinhold, S. L., et al. *The FASEB Journal* 4(2):208–214 (1990).
Wymann, M. P., et al. *The Journal of Biological Chemistry* 264(27):15829–15834 (1989).
Dewald, B. et al., *The Journal of Biological Chemistry* 263(31):16179–16184 (1988).
Haeflinger, W., et al., *Helv. Chem. Acta*, 56(8):2901–2904 (1973).
MacMillan, J. et al., *J. Chem. Soc.* Perkin I, 2892–2898 (1972).
Abbas, H. K. et al., *Appl. Environ. Microbiol.* 54(5):1268–1274 (1988).
Nakanishi, S., et al., *J. Biol. Chem.*, 267(4):2157–2163 (1992).
Ohara–Imaizumi, M., et al., *Biochem. Biophys. Res. Commun.*, 185(3):1016–1021 (1992).
Coughlin, S. R. et al., *Science*, 243:1191–1194 (1989).
Baggiolini, M., et al., *Exp. Cell Res.*, 169:408–418 (1987).
Matter, W. F. et al., *Biochem. Biophys. Res. Commun.* 186(2):624–631 (1992).
Shibasaki, F. et al., *J. Biol. Chem.*, 266(13):8108–8114 (1991).
Kaplan, D. R. et al., *Cell*, 50:1027–1029 (1987).
Valius, M., et al., *Cell*, 73:321–334 (1993).

*Primary Examiner*—Nicky Chan
*Attorney, Agent, or Firm*—James J. Sales; Gerald V. Dahling

[57] ABSTRACT

Wortmannin and certain of its analogs are inhibitors of bone loss/bone resorption and cartilage degradation.

4 Claims, No Drawings

METHODS FOR INHIBITING BONE LOSS AND CARTILAGE DEGRADATION USING WORTMANNIN AND ITS ANALOGS

This application is a division of application Ser. No. 08/112,012, filed Aug. 25, 1993, abandoned.

BACKGROUND OF THE INVENTION

This invention relates to a new method for treating vertebrates suffering from diseases associated with increased bone or cartilage resorption, involving the therapeutic use of wortmannin and analogs thereof.

The current major diseases or conditions of bone which are of public concern include post-menopausal osteoporosis, hysterectomy patients, senile osteoporosis, patients undergoing long-term treatment of corticosteroids, side effects from glucocorticoid or steroid treatment, patients suffering from Cushings's syndrome, gonadal dysgensis, periarticular erosions in rheumatoid arthritis, osteoarthritis, Paget's disease, osteohalisteresis, osteomalacia, hypercalcemia of malignancy, osteopenia due to bone metastases, periodontal disease, and hyperparathyroidism.

All of these conditions are characterized by bone loss, resulting from an imbalance between the degradation of bone (bone resorption) and the formation of new healthy bone. This turnover of bone continues normally throughout life and is the mechanism by which bone regenerates. However, the conditions stated above will tip the balance towards bone loss such that the amount of bone resorbed is inadequately replaced with new bone, resulting in net bone loss.

One of the most common bone disorders is post-menopausal osteoporosis which affects an estimated 20 to 25 million women in the United States alone. Women after menopause experience an increase in the rate of bone turnover with resulting net loss of bone, as circulating estrogen levels decrease. The rate of bone turnover differs between bones and is highest in sites enriched with trabecular bone, such as the vertebrae and the femoral head. The potential for bone loss at these sites immediately following menopause is 4–5% per year. The resulting decrease in bone mass and enlargement of bone spaces leads to increased fracture risk, as the mechanical integrity of bone deteriorates rapidly.

At present, there are 20 million people with detectable vertebral fractures due to osteoporosis and 250,000 hip fractures per year attributable to osteoporosis in the U.S. The latter case is associated with a 12% mortality rate within the first two years and 30% of the patients will require nursing home care after the fracture. Therefore, bone disorders are characterized by a noticeable mortality rate, a considerable decrease in the survivor's quality of life, and a significant financial burden to families.

Essentially all of the conditions listed above would benefit from treatment with agents which inhibit bone resorption. Bone resorption proceeds by the activity of specialized cells called osteoclasts. Osteoclasts are unique in their ability to resorb both the hydroxyapatite mineral and organic matrix of bone. They are identical with the cartilage resorbing cells, previously termed Chondroclasts. It is for this reason that potent inhibitors of osteoclastic bone resorption will also inhibit the cell-mediated degradation of cartilage observed in rheumatoid arthritis and osteoarthritis.

Therapeutic treatments to impede net bone loss include the use of estrogens. Estrogens have been shown clearly to arrest the bone loss observed after menopause and limit the progression of osteoporosis; but patient compliance has been poor because of estrogen side-effects. These side effects include resumption of menses, mastodynia, increase in the risk of uterine cancer, and possibly an increase in the risk of breast cancer.

Alternatively, calcitonin has been used to treat osteoporotic patients. Salmon calcitonin has been shown to directly inhibit the resorption activity of mammalian osteoclasts and is widely prescribed in Italy and Japan. However, calcitonins are prohibitively expensive to many and appear to be short-lived in efficacy. That is, osteoclasts are able to "escape" calcitonin inhibition of resorption by down-regulating calcitonin receptors. Therefore, recent clinical data suggests that chronic treatment with calcitonin is ineffective to arrest the post-menopausal loss of bone.

SUMMARY OF THE INVENTION

The invention provides a method of inhibiting bone resorption, bone loss, and cartilage degradation in a subject comprising administering to said subject a pharmaceutically effective dose of a compound selected from the group of

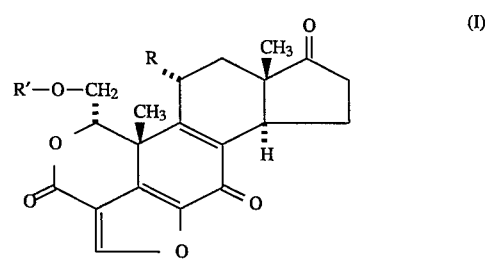

(I)

wherein R is hydrogen or acetoxy, and R' is $C_1$–$C_6$ alkyl;

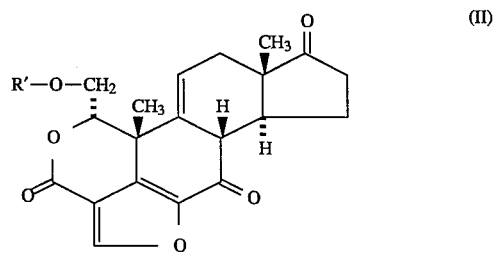

(II)

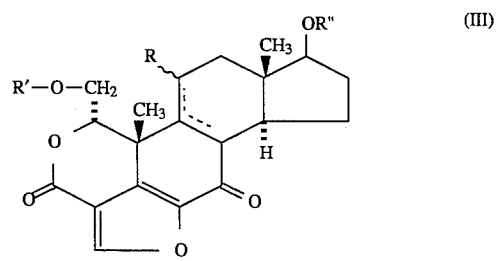

(III)

wherein R" is hydrogen, $C_1$–$C_6$ alkyl or

wherein R''' is hydrogen or $C_1$–$C_6$ alkyl;

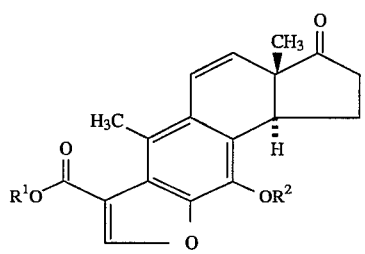

(IV)

wherein $R^1$ is hydrogen, methyl, or ethyl; and $R^2$ is hydrogen or methyl; or a pharmaceutically acceptable salt of any of the above. Also, the invention provides the novel compound 11-desacetoxy-17α-dihydrowortmannin (IIIb).

DETAILED DESCRIPTION OF THE INVENTION

The current invention concerns the discovery that Wortmannin and its analogs are useful in the inhibition of bone lose/resorption and cartilage degradation. The following compounds are encompassed by the invention:

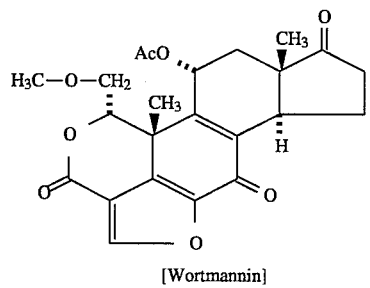

(Ia)

[Wortmannin]

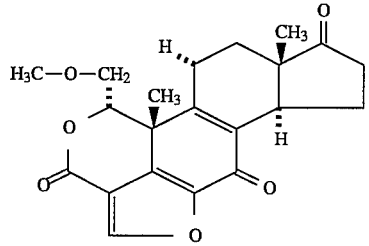

(Ib)

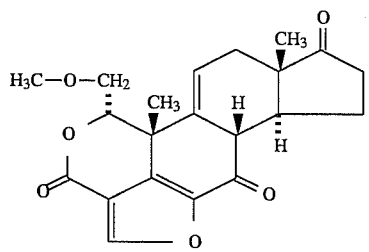

(II)

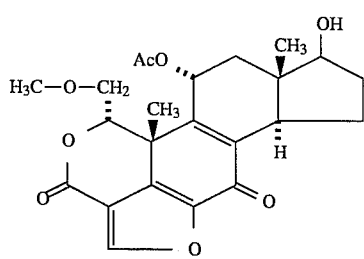

(IIIa)

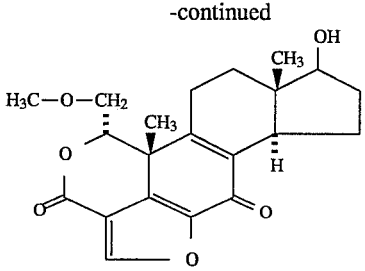

(IIIb)

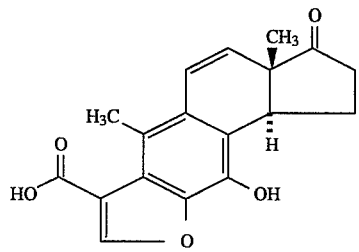

(IVa)

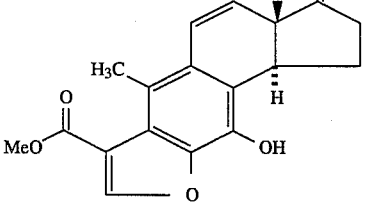

(IVb)

TABLE 1

Wortmannin and Analogs

| Formula Designation | R | $R^1$ | $R^2$ | R | Trivial Name |
|---|---|---|---|---|---|
| Ia | acetoxy | NA | NA | NA | wortmannin |
| Ib | H | NA | NA | NA | 11-desacetoxy-wortmannin |
| II | NA | NA | NA | NA | Δ9,11-dehydro-desacetoxy-wortmannin |
| IIIa | acetoxy | NA | NA | H | 17α-dihydro-wortmannin |
| IIIb | H | NA | NA | H | 11-desacetoxy-17α-dihydrowortmannin |
| IVa | NA | H | H | NA | opened A-ring acid of wortmannin |
| IVb | NA | methyl | H | NA | opened A-ring methyl ester of wortmannin |

The biosynthetic production of wortmannin (Ia) is well known in the art and the analogs are synthesized from wortmannin. Typically, wortmannin is produced by the fermentation of any one of a number of previously disclosed microorganisms such as *Talaromyces wortmannin* [Nakanishi, et al., J. Biol. Chem., 267 (4): 2157–2163 (1992)]; and *Penicillium wortmannii, Myrothecium roridium,* and *Fusarium oxysporum* [Abbas, et al., Apply. Environ. Microbiol., 54(5): 1267–1274 (1988)]. Following fermentation, wortmannin is extracted and purified via known methods.

Preferably, wortmannin is microbially synthesized and isolated in substantially pure form from a fermentation culture identified as A24603.1.

Culture A24603.1 has been deposited in compliance with the Budapest Treaty, and made part of the stock culture collection of the Midwest Area Northern Regional Research Center, Agricultural Research Service, United States Department of Agriculture, 1815 North University Street, Peoria, Ill., 61604. The accession number is NRRL 2112, (*Penicillium duclauxii*).

The permanency of the deposit of this culture at the Midwest Area Northern Regional Research Center at Peoria, Ill., and ready accessibility thereto by the public will be afforded throughout the effective life of the patent in the event the patent is grated. Access to the culture will be available during pendency of the application under 37 C.F.R. §1.14 and 35 U.S.C. §112. All restrictions on the availability to the public of the culture will be irrevocably removed upon granting of the patent.

Wortmannin is produced by culturing the above-referenced A24603.1 strain under submerged aerobic conditions in a suitable culture medium until a recoverable amount of wortmannin is produced. Wortmannin can be recovered using various isolation and purification procedures understood in the art.

The medium used to grow the A24603.1 culture can be any one of a number of media. For economy in production, optimal yield, and ease of product isolation, however, preferred carbon sources in large-scale fermentation are glucose and soluble starch such as corn starch. Maltose, ribose, xylase, fructose, galactose, mannose, mannitol, potato dextrin, methyl oleate, oils such as soybean oil and the like can also be used.

Preferred nitrogen sources are enzyme-hydrolyzed casein and cottonseed flour, although pepsinized milk, digested soybean meal, fish meal, corn steep liquor, yeast extract, acid-hydrolyzed casein, beef extract, and the like can also be used.

Among the nutrient inorganic salts which can be incorporated in the culture media are the customary soluble salts capable of yielding calcium, magnesium, sodium, ammonium, chloride, carbonate, sulfate, nitrate, zinc, and like ions.

Essential trace elements necessary for the growth and development of the organism also should be included in the culture medium. Such trace elements commonly occur as impurities in other substituents of the medium in amounts sufficient to meet the growth requirements on the organism.

For production of substantial quantities of wortmannin, submerged aerobic fermentation in stirred bioreactors is preferred. Small quantities of wortmannin may be obtained by shake-flask culture. Because of the time-lag in production commonly associated with inoculation of large bioreactors with the spore form of the organism, it is preferable to use vegetative inoculum. The vegetative inoculum is prepared by inoculating a small volume of culture medium with the spore form or mycelial fragments of the organism to obtain a fresh, actively growing culture of the organism. The vegetative inoculum medium can be the same as that used for larger fermentations, but other media are also suitable.

Wortmannin is produced by the A24603.1 organism when grown at temperatures between about 23° and 29° C. Optimum temperature for wortmannin production appears to be about 25° C.

As is customary in submerged aerobic culture processes, sterile air is blown into the vessels from the bottom while the medium is stirred with conventional turbine impellors. In general, the aeration rate and agitation rate should be sufficient to maintain a level of dissolved oxygen of at least 45% of air saturation with an internal vessel pressure of about 5 atmospheres.

Following its production, wortmannin can be recovered from the fermentation medium by methods used in the art. The wortmannin produced during fermentation of the A24603.1 organism occurs mainly in the broth.

Typically, wortmannin can be recovered from the biomass by a variety of techniques. A preferred technique involves filtering while fermentation broth with a ceramic filter. The filtrate is eluted with an organic solvent such as ethyl acetate and concentrated. The concentrate is suspended in alcohol until crystallization occurs and the solution is filtered, washed and dried. For confirmation, the crystalline material is dissolved in an organic solvent and chromatographed on a reverse-phase silica gel absorbent ($C_8$ or $C_{18}$). Fractions are eluted in an organic-aqueous buffer such as 60% acetonitrile.

11-deacetoxywortmannin (formula Ib) also is known in the art as are methods for its preparation. Generally, this compound can be biosynthetically produced by fermenting a culture of *Penicillium funiculosum Thom* [see, e.g., Baggolini, et al., *Exp. Cell Res.*, 169: 408–418 (1987)]; but, preferably, is chemically derived from wortmannin by the method disclosed by Haeflinger, et al., *Helv. Chem. Acta*, 56(8): 2901–2904 (1973).

Similarly, the preparation of Δ9,11-dehydrodesacetoxywortmannin (formula II) is known in the art and is described by Haeflinger, et al., supra; and the preparation of compounds of formula IV is described by MacMillan, J., et al., *J. Chem. Soc, Perkin I*: 2891–2898 (1972). The preparation of compounds of the formula III maybe prepared by methods known in the art, and are exemplified in the preparation examples, herein. When R" is

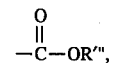

the compounds may be prepared in an analogous fashion to that described in Ott et al., *J. Am Chem. Soc.* 74, p. 1239 (1952).

For therapeutic treatment of the specified indications, a compound of formula I, II, III or IV may be administered as such, or can be compounded and formulated into pharmaceutical compositions in unit dosage form for parenteral, transdermal, rectal, nasal or intravenous administration or, preferably, oral administration. Such pharmaceutical compositions are prepared in a manner well known in the art and comprise at least one active compound selected from the group consisting of compounds of formulae I, II, III, and IV associated with a pharmaceutically carrier. The term "active compound", as used throughout this specification, refers to at least one compound selected from compounds of the formulas or pharmaceutically acceptable salts thereof.

The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevnt circumstances including the condition to be treated, the choice of compound to be administered, and the chose route of administration, and therefore the above dosage ranges are not intended to limit the scope of the invention in any way.

In such a composition, the active compound is known as "active ingredient". In making the compositions, the active ingredient will usually by mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 0.04 to about 900 mg and, more frequently, from about 1 to about 500 mg of the active ingredient. The term "unit dosage form" refers to physically discreet units suitable as unitary dosages for human subjects and other mammals, each unit containing a predetermined quantity of active material calculated to produce the desired therapeutic effect, in association with the required pharmaceutically acceptable carrier, diluent or excipient must be compatible with the other ingredients of the formulation and not deleterious to the recipient thereof.

The following formulation examples are illustrative only and are not intended to limit the scope of the invention in any way. The meaning of the term "active ingredient" is as defined above.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The compounds are blended and compressed to form tablets each weighing 665 mg.

Formulation 3

An aerosol solution is prepared containing the following components:

|  | Weight |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  |  |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient(s) | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 mL |

PREPARATION 1

Fermentation of Culture A24603.1

A. Shake-Flask

The culture A24603.1, either as a lyophilized pellet or as a suspension maintained in liquid nitrogen, is used to inoculate a vegetative medium having the following composition

| Vegetative Medium | |
|---|---|
| Ingredient | Amount (g/L) |
| Glucose | 10.0 |
| Glycerol | 10.0 |
| Cottonseed Flour[a] | 25.0 |

Unadjusted pH=6.3; no adjustment
[a] PROFLO Flour (Traders Protein, Memphis, Tenn.).

The inoculated vegatetive medium was incubated in a 250 mL wide-mouth Erlenmeyer flask at 25° C. for about 72 hours on a shaker orbiting in a two-inch (5.08 cm) circle at 250 rpm.

B. Tank Fermentation of Culture A24603.1

In order to provide a larger volume of inoculum, 10 mL of incubated shake-flask medium, prepared as described in Section A, was used to inoculate 400 mL of a second-stage vegetative medium having the same composition as described above. This second-stage medium was incubated in a 2-L wide-mouth Erlenmeyer flask at 25° C. for about 23 hours on a shaker orbiting in a two-inch (5.08 cm) circle at 250 rpm.

This second-stage medium (400 mL) was used to inoculate 115 L of sterile production medium having the following composition.

| Production Medium | |
|---|---|
| Ingredient | Amount (g/L) |
| Glucose | 25.0 |
| Corn Starch | 10.0 |
| Lexein | 10.0 |
| Enzyme-hydrolyzed casein | 4.0 |
| Blackstrap molasses | 5.0 |
| $MgSO_4$ (anhydrous) | 5.0 |
| $CaCO_3$ | 2.0 |
| Deionized $H_2O$ | q.s. to 115 L |
| Unadjusted pH = 6.8; no adjustment. | |
| Antifoam agent added: SAG 471[b] (0.2 gm/L). | |

[a] NZ Amine A (Sheffield Chemical Co., Norwich, NY).
[b] SAG 471 (Union Carbide, Sistersville, WV).

The inoculated production medium was allowed to ferment in a 115-L stirred fermentation tank for 4–5 days at a temperature of about 25° C. A dissolved oxygen level of about 45% of air saturation was maintained, as was a low rpm (180–330) in the stirred vessel.

PREPARATION 2

Isolation and Purification of Wortmannin

Fermentation broth from Preparation 1 was filtered through a ceramic filter (Membralox Systems, Illinois Water Treatment, Rockford, Ill.) to yield 175 L of filtrate containing wortmannin. The pH of the filtrate was then eluted three times with one-half volumes of ethyl acetate to give a combined volume of 207 L which was concentrated to 6 L in vacuo.

The 6 L of ethyl acetate concentrate was further concentrated in vacuo to form a dark brown viscous oil to which 500 mL of methanol was added. The mixture was swirled until the resulting crystallization was complete, filtered, briefly washed with cold methanol and dried in vacuo to give 20.4 g of wortmannin.

The methanol supernatant was reconcentrated in vacuo to form a viscous oil, dissolved in 180 mL of chloroform and applied to a 12×20 cm column of Woelm Grade 62 silica in chloroform. 5.0 L of chloroform wash was concentrated in vacuo to form a brown oil which was then dissolved in 250 mL of warm methanol. The resulting crystals were collected after 18 hours, via filtration, giving 4.2 g of wortmannin. The crystallization procedure was repeated on the remaining supernatant, yielding an additional 1.9 g of wortmannin. The identity of wortmannin was confirmed by HPLC.

PREPARATION 3

17α-Dihydrowortmannin

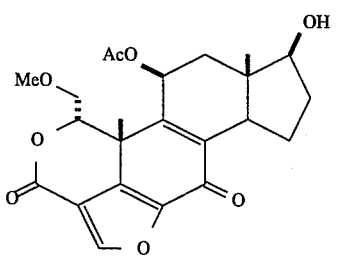

(IIIa)

To a solution of wortmannin (100 mg) stirring in THF at −78° C. was added diisobutylaluminum hydride (0.4 mL of a 1.0 M solution in toluene, 0.4 mmol). After 0.5 h, the reaction was quenched with saturated aqueous $NaHCO_3$. The mixture was then warmed to room temperature and extracted with $CH_2Cl_2$. The combined organic extracts were washed with brine and dried ($MgSO_4$). The crude material was purified by radial chromatography ($SiO_2$, 4 mm, 9:1 EtOAc/Hexanes) to give 17α-dihydrowortmannin as an off-white powder.

$^1$H NMR (300 MHz, $CDCl_3$) 8.22 (s, 1H), 6.10 (m, 1H), 4.76 (dd, 1H), 3.88 (t, 1H), 3.44 (dd, 1H), 3.20 (s, 3H), 2.95 (½ABq. 1H), 2.75 (m, 1H), 2.62 (½ABq, 1H), 2.52 (m, 1H), 210–2.30 (m, 4H), 1.4–1.7 (m), 0.85 (s, 3H), MS FD$^+$ 431, IR (Cell, $CDCl_3$), 1751, 1680 cm-1).

PREPARATION 4

11-Desacetoxy-17α-dihydrowortmannin

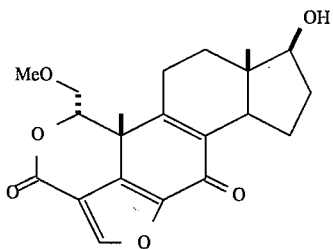

(IIIb)

To a solution of compound IB (15 mg) (prepared via the method of Haefloger, W.; Hauser, D. Helv. Chim. Acta, 56, 2901, (1973)) stirring in THF at −78° C. was added diisobutylaluminum hybride (0.1 mL of a 1.0 M solution in toluene). After 1 h, the reaction was quenched with saturated aqueous $NaHCO_3$. The mixture was then warmed to room temperature and extracted with $CH_2Cl_2$. The combined organic extracts were washed with brine and dried ($MgSO_4$). The crude material was purified by radial chromatography ($SiO_2$, 1 mm, 9:1 EtOAc/Hexanes) to give the titled product as a tan powder. $^1$H-NMR (300 MHz, $CDCl_3$) 8.19 (s, 1H), 4.81 (t, 1H), 3.80 (t, 1H), 3.15 (s, 3H), 1.7 (s, 3H), 0.7 (s, 3H). MS FAB$^+$ 373.3.

Drugs which prevent bone loss and/or add back lost bone may be evaluated in the ovariectomized rat. This animal model is well established in the art (see, for example, Wronski, et al. (1985) Calcif. Tissue Int 37:324–328; Kimmel, et al. (1990) Calcif. Tissue Int. 46:101–110; and Durbridge, et al. (1990) Calcif. Tissue Int. 47:383–387; these references are hereby incorporated in their entirety) Wronski, et al. ((1985) Calcif. Tissue Int. 43:179–183)) describe the relationship between bone loss and bone turnover in the ovariectomized rate model.

Also established in the art is the acute rat in vivo model assay (Thompson et al., Endocrinology, 97 pp. 283–289 (1975); Rasmussen, Calc. Tiss. Res., 23, pp. 87–94 (1977); Sammon et al., Am. J. of Physiology; 218, No. 2, pp. 479–485 (1970); Hargis et al., Endo. 94, No. 6 pp. 1644–1649 (1974); Thomas et al., Bone and Mineral, 4, pp. 73–82 (1988); and Au et al., Am. J. Physiol., 109, No. 3, pp. 637–642 (1965)).

EXAMPLE 1

Wortmannin was found to inhibit the in vitro bone resorption activity of hen osteoclasts with IC50=300 nM (as carried out according to Sato et al., "Echistatin is a Potent Inhibitor of Bone Resorption in Culture", J. Cell Biol. 111, pp. 1713–1723 (1990)) and rat osteoclasts with IC50=50 nM, (as carried out according to Sato and Grasser, "Effects of Bisphosphonates on Isolated Rat Osteoclasts as Examined by Reflected Light Microscopy", J. Bone and Mineral Research, 5, pp. 31–40, (1990), as shown in Tables 2a and 2b. Data presented are percent of control bone resorption (n=3–6, mean ±SE). Control bone resorption varied from 17–47 mg of bone resorbed between days 4–6 in culture (Table 2a). Control resorption in Table 2b corresponded to 12–62 Howship's lacunae per bone slice (n=4–4. mean ±SE).

TABLE 2a

| % Control Bone Resorption | Wortmannin Concentration (M) |
| --- | --- |
| 90 ± 7 | $1 \times 10^{-8}$ |
| 79 ± 2 | $5 \times 10^{-8}$ |
| 58 ± 6 | $1 \times 10^{-7}$ |
| 52 ± 3 | $5 \times 10^{-7}$ |
| 54 ± 4 | $1 \times 10^{-6}$ |
| 19 ± 1 | $5 \times 10^{-6}$ |
| 23 ± 7 | $1 \times 10^{-5}$ |

TABLE 2b

| % Control Bone Resorption | Concentration (M) |
| --- | --- |
| 93 ± 11 | $1 \times 10^{-10}$ |
| 79 ± 22 | $1 \times 10^{-9}$ |
| 32 ± 13 | $1 \times 10^{-8}$ |
| 30 ± 6 | $1 \times 10^{-7}$ |
| 3 ± 3 | $1 \times 10^{-6}$ |

EXAMPLE 2

As summarized in Table 3, the various analogs inhibited the resorption of hen osteoclasts with IIIA IC50=10 nM; IIIb, IC50=100 nM; and Ib, IC50=500 nM. Data presented are percent of control bone resorption (n=3–6, mean ±SE). Control levels of resorption varied from 26–49 mg bone resorbed between days 4–6 in culture.

TABLE 3

| Concentration | IIIa | IIIb | Ib | IVa |
| --- | --- | --- | --- | --- |
| $1 \times 10^{-9}$ | 94 ± 5 | 124 ± 23 | 106 ± 10 | 93 ± 14 |
| $1 \times 10^{-8}$ | 67 ± 5 | 88 ± 19 | 97 ± 17 | 99 ± 15 |
| $1 \times 10^{-7}$ | 29 ± 4 | 50 ± 4 | 90 ± 15 | 110 ± 13 |
| $1 \times 10^{-6}$ | 8 ± 1 | 26 ± 3 | 42 ± 3 | 105 ± 10 |

EXAMPLE 3

Compounds were also examined in a rat model of secondary hyperparathyroidism according to similars method as set out in Thomas et al., *Bone and Mineral*, 4, pp. 73–82 (1988) in an effort to examine the ability of these compounds to inhibit osteoclastic bone resorption in vivo. Serum calcium levels (mg/dl) were previously shown to be dependant on bone resorption in Sprague Dawley rats (400 g males) maintained on a calcium deficient diet for 2 weeks. Serum calcium levels were examined colorimetrically (Sigma, St. Louis) before (T=0) and after 6 hr infusion (T=6) of compounds at a rate of 0.08 ml/hr through cannula inserted into the jugular vein of anesthesized rates. At T=0, the serum calcium of a control rat was 12 mg/dl. Wortmannin and IIIa were effective in significantly (P<0.05) lowering serum calcium after 6 hr of infusion at 1 mg/kg/day (16 ug/hr for 400 g rat), to approximately 9 and 5 mg/dl of serum calcium, respectively, as compared to the positive control of salmon calcitonin (12 ug/kg/day), which lowered calcium serum to 9 mg/dl (P<0.05).

EXAMPLE 4

As summarized in Table 4, IIIa was also examined in 6 month old, ovariectomized rats. The bone mineral density (mg/cm³) and bone mineral content (mg) of the left proximal tibiae were quantitated by computer tomography with a Norland 960 pQCT after daily dosing per os for 5 weeks, similar to the methods of Griffin et al., "Dual-energy X-ray Absorptiometry of the Rat: Accuracy, Precision and Measurement of Bone Loss", *J. Bone Miner. Res* 8, pp. 795–800 (1993). There were five groups of rats with n=6 per group: Sham, OVX, 0.001, 0.01, and 0.1 mg of IIIa/kg per os daily. In vivo data are presented for a 2 mm slice of the left proximal tibia at 5 weeks post-ovariectomy (mean ± standard deviation).

TABLE 4

| | Proximal Tibiae | |
| --- | --- | --- |
| Group (n = 6) | Total Bone Mineral Density (mg/cm3) | Bone Content (mg) |
| Sham | 590 ± 26 | 14 ± 1.5 |
| OVX | 494 ± 29 | 10.4 ± 1.2 |
| 0.001 mg/kg/day | 528 ± 33 | 13.6 ± .6 |
| 0.01 mg/kg/day | 545 ± 26 | 13.5 ± 1 |
| 0.1 mg/kg/day | 494 ± 18 | 11.5 ± .7 |

We claim:
1. A method of inhibiting bone resorption in a subject comprising administering to said subject a pharmaceutically effective dose of a compound selected from

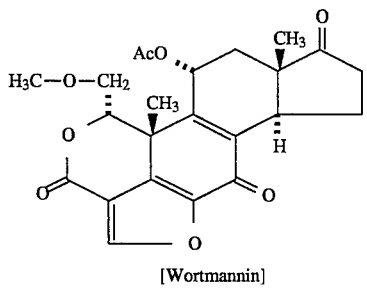
[Wortmannin] (Ia)

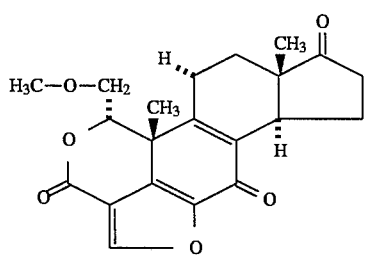
(Ib)

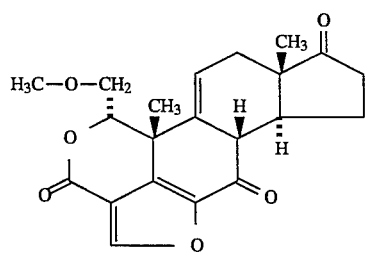
(II)

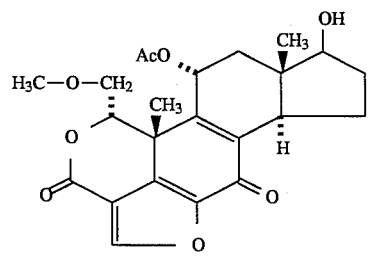
(IIIa)

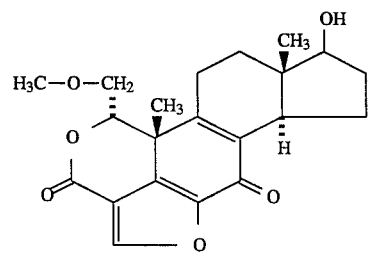
(IIIb)

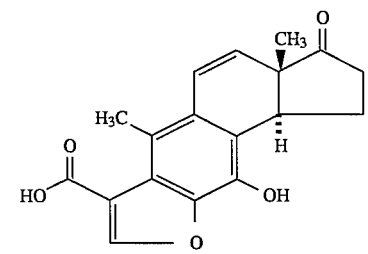
(IVa)

-continued and

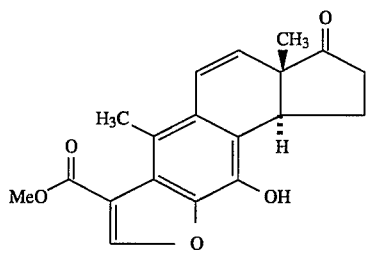
(IVb)

or a pharmaceutically acceptable salt thereof.

2. A method of inhibiting cartilage degradation in a subject comprising administering the said subject a pharmaceutically effective dose of a compound selected from

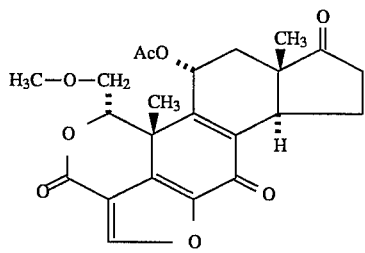
(Ia)
[Wortmannin]

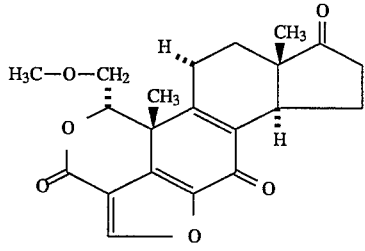
(Ib)

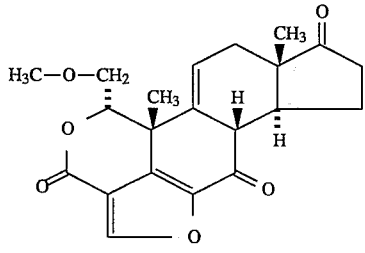
(II)

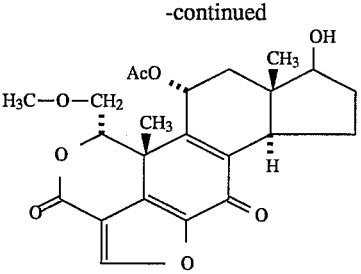
(IIIa)

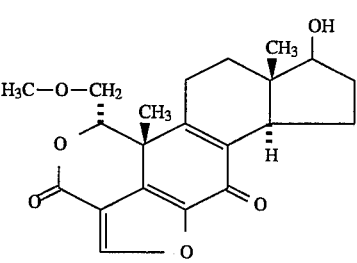
(IIIb)

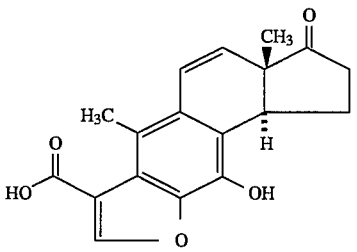
(IVa)

and

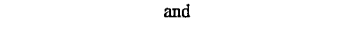
(IVb)

or a pharmaceutically acceptable salt thereof.

3. The method of claim 1 wherein said subject has or is susceptible to osteoporosis.

4. The method of claim 1 wherein the compound is administered prophylactically.

* * * * *